United States Patent [19]

Money

[11] 4,320,763
[45] Mar. 23, 1982

[54] PROTECTION DEVICE FOR PACEMAKER IMPLANTEES

[75] Inventor: David Money, Pennant Hills, Australia

[73] Assignee: Telectronics Pty. Limited, Lane Cove, Australia

[21] Appl. No.: 83,522

[22] Filed: Oct. 10, 1979

[51] Int. Cl.³ .............................................. A61N 1/36
[52] U.S. Cl. .............................. 128/419 PG; 128/908
[58] Field of Search .............. 128/419 P, 419 PG, 908

[56] References Cited

U.S. PATENT DOCUMENTS 3,605,728  9/1971  Ogle .................................... 128/908
3,968,802  7/1976  Ballis ............................ 128/419 PG Primary Examiner—William E. Kamm
Attorney, Agent, or Firm—Finnegan, Henderson, Farabow, Garrett and Dunner

[57] ABSTRACT

A current-limiter device is placed in series circuit between a pacemaker and the proximal end of an electrode to prevent tissue damage adjacent the distal end of the electrode which otherwise may have occurred during defibrillation, cardioversion, or diathermy.

6 Claims, 5 Drawing Figures

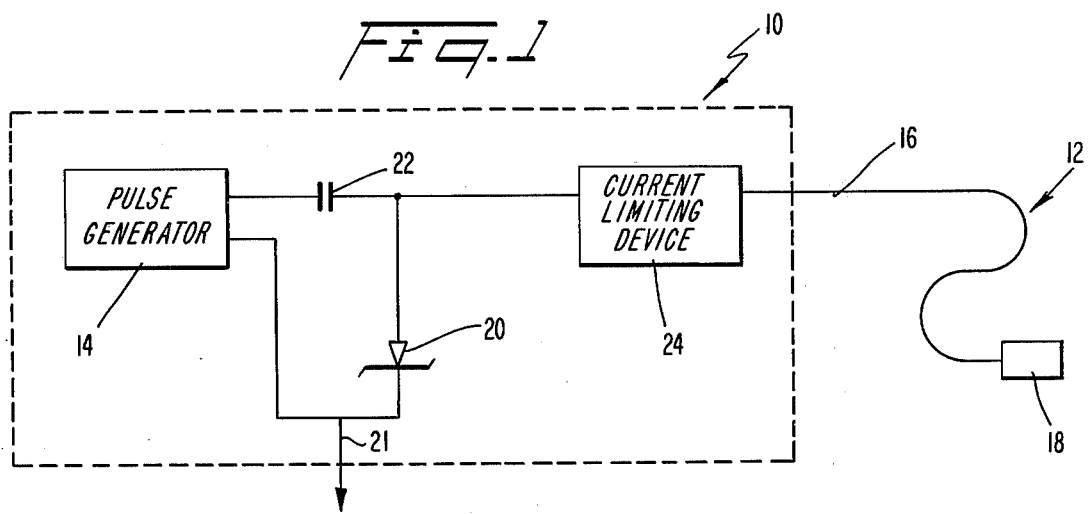
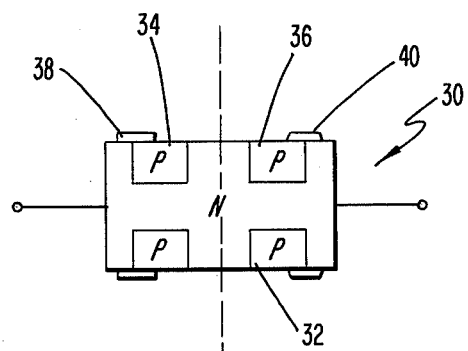
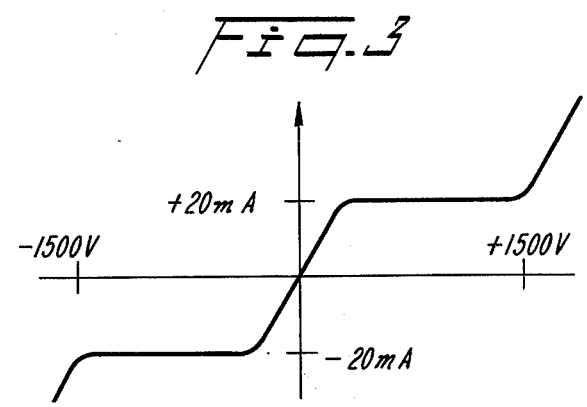
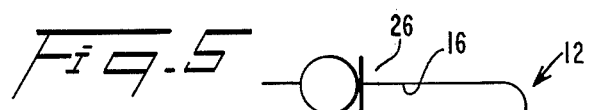
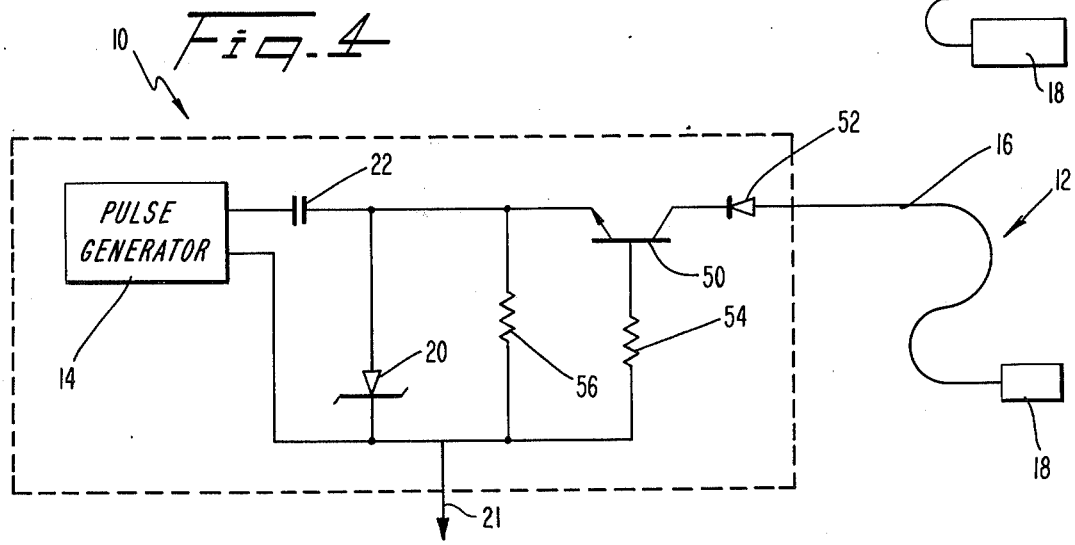

PROTECTION DEVICE FOR PACEMAKER IMPLANTEES

BACKGROUND OF THE INVENTION

I. Field of the Invention

The present invention relates to apparatus used to stimulate body tissue, including cardiac pacemakers.

II. Background of the Invention

Packmakers are well-known to comprise pulse-generating circuits when periodically deliver electrical pulse to the proximal end of an electrode. The distal end of the electrode contains an exposed conductive tip and is placed adjacent muscle tissue of the heart. The electrode thereby operates to deliver the pulses from the pacemaker to the heart to stimulate the heart.

All humans, including implantees of pacemakers, are subject to being exposed to externally high voltages. For example, if ventricular fibrillation, an abnormal rhythm of the heartbeat, should occur, one means of securing return to a normal rhythm is to apply a pair of conductive paddles to the exterior of the body and place a high voltage across the paddles. The resultant current flow through the heart often reverts the heart to a normal rhythm. This process is called defibrillation. Defibrillation can even be used to start a stopped heart.

Cardioversion is a more general term of the process of exposing the heart to a high current to correct arrhythmias.

Diathermy is another process by which high currents are introduced to the human body. Diathermy is the process wherein an electrical current is concentrated at a point on a body to cut tissue and arrest bleeding. In each of these situations, defibrillation, cardioversion, and diathermy, when a pacemaker is inside the patient, a current goes through the pacemaker and associated electrode because the pacemaker and associated electrode are more conductive than the surrounding body tissue. The known prior art recognizes that such a current through the pacemaker and associated electrode could cause an adverse effect on the operation of the pacemaker. Accordingly, the known prior art places one or more Zener diodes or similar devices between the output and indifferent terminals or ground of the pacemaker. This arrangement limits the amount of current and voltage surge which may be introduced from the electrode into the pacemaker upon application of high voltages to the exterior of the patient's body.

While such prior art arrangements protect the circuitry of the pacemaker, there is no limitation on the current flow which is permitted along the electrode and in particular which is permitted to flow between the distal tip of the electrode and the heart tissues adjacent that tip. This current flow has been found to cause considerable damage. First, the current may damage the heart itself. Second, the current can increase the pacing threshold of the heart, which is the amount of electrical signal required from the pacemaker to stimulate the heart. Specifically, this current can cause fibrosis of the tissue adjacent the electrode tip and thereby increase the distance between the electrode tip and excitable heart tissue.

It is, therefore, an object of the present invention to protect the heart tissue of a pacemaker implantee from damage upon application of high voltages to the user's body as may occur with defibrillation, cardioversion, or diathermy.

Additional objects and advantages of the invention will be set forth in part in the description which follows, and in part will be obvious from the description or may be learned by practice of the invention. The objects and advantages of the invention may be realized and obtained by means of the instrumentalities and combinations particularly pointed out in the appended claims.

SUMMARY OF THE INVENTION

To achieve the foregoing objects, and in accordance with the purposes of the invention, as embodied and broadly described herein, there is provided an improvement for a pacemaker assembly comprising pulse-generating means for generating electrical pulses and electrode means having a proximal end coupled to said pulse-generating means and having a distal end designed to be placed adjacent to body tissue for delivering the pulses to the body tissue. The improvement of the present invention comprises a current-limiting device coupled in series with the pulse-generating means and electrode means for protecting the tissue against high current flow between the distal end of the electrode means and the body tissue, as may occur, for example, with defibrillation, cardioversion, or diathermy. The current-limiting device may, for example, comprise a current-limiting diode, a series-connected pair of FET's or the emitter-collector path of a transistor in series with a diode. The current-limiting device preferably limits current flow between the distal end of the electrode means and the body tissue to 20 mA even when voltage applied to the exterior of the pacemaker assembly is a great as 1500 volts.

In another sense, the present invention comprises a pacemaker circuit for generating electrical pulses, the pacemaker circuit including a pulse generator to supply pulses to a proximal end of an electrode, the electrode having a distal end designed to be placed adjacent to body tissue for delivering the pulses to the body tissue, the pacemaker circuit further including a circuit coupled between said pulse generator and the electrode for protecting the tissue against high current flow between the distal end of the electrode and the tissue as may occur with defibrillation, cardioversion, or diathermy.

BRIEF DESCRIPTION OF THE DRAWINGS

The accompanying drawings, which are incorporated in and constitute a part of the specification, illustrate a preferred embodiment of the invention, and together with the general description of the invention given above and the detailed description of the preferred embodiment given below, serve to explain the principles of the invention.

FIG. 1 illustrates a protection device for pacemaker users in accordance with the teachings of the present invention;

FIG. 2 is a diagrammatic cross-sectional view of a current-limiting device for use in accordance with the teachings of the present invention;

FIG. 3 is a diagram of current vs. voltage characteristics of the current-limiting device illustrated in FIG. 2;

FIG. 4 is a schematic diagram of another example of a protection device for pacemaker implantees employing the teachings of the present invention; and FIG. 5 shows a current-limiting diode for use as the protection device of FIG. 1.

The above general description and the following detailed description are merely illustrative of the generic invention and additional modes, advantages and particulars of this invention will be readily suggested to those skilled in the art without departing from the spirit and scope of the invention.

DESCRIPTION OF THE PREFERRED EMBODIMENT

Reference will now be made in detail to the present preferred embodiment of the invention as illustrated in the accompanying drawings.

Broadly, the present invention relates to an improvement for a pacemaker assembly, which assembly comprises pacemaker means for generating electrical pulses and electrodes means having a proximal end coupled to said pacemaker means and a distal end designed to be placed adjacent to body tissue for delivering the pulses to the tissue.

For example, as illustrated in FIG. 1, a pacemaker assembly may comprise a pacemaker 10 and an electrode 12.

As is well known to those skilled in the art, pacemaker assembly 10 may comprise a pulse generator 14 which periodically delivers electrical pulses to the proximal end 16 of electrode 12. The distal end 18 of electrode 12 contains an exposed conductive tip which is placed adjacent to muscle tissue of the heart. The electrode 12 thereby operates to deliver pulses from pulse generator 14 to the heart to stimulate the heart.

The known prior art recognizes that excessive current developed in electrode 12 upon introduction of high voltages to the exterior of a patient using pacemaker assembly 10 could cause an adverse effect on the operation of pacemaker assembly 10. Accordingly, the known prior art places one or more Zener diodes 20 or similar devices between the output and indifferent terminals or ground 21 of pulse generator 14. These diodes must typically be capable of handling current loads in the range of one to five amperes. Furthermore capacitor 22 may be coupled between diode 20 and pulse generator 14 to further isolate pulse generator 14 from the effect of excess current in electrode 12.

While this prior art arrangement protects the circuitry of pulse generator 14 from voltage overloads, there is no limitation on the current which is permitted to flow along electrode 12 and in particular between distal tip 18 of electrode 12 and the heart tissue adjacent to tip 18.

In order to prevent potential damage to the tissue surrounding the distal tip of the electrode, and in accordance with the present invention, a pacemaker assembly is improved by the inclusion of a current-limiting device coupled in series between the pulse generator means of the pacemaker assembly and the electrode means for protecting said tissue against high current flow between the distal tip of the electrode means and the tissue as may occur with defibrillation, cardioversion, or diathermy.

As illustratively shown in FIG. 1, a current-limiting device 24 is shown coupled between pulse generator 14 and the proximal end 16 of electrode 12. Current-limiting device 24 prevents damage to tissue adjacent distal tip 18 by limiting the amount of current which can pass through pacemaker assembly 10 and electrode 12 during application of high voltage levels to the human body. Thus, current-limiting device 24 protects the implantee as well as the pacemaker assembly 10 from adverse effects of high current loads during defibrillation, cardioversion, or diathermy. Current-limiting device 24 must be chosen to maintain the current flow through electrode 12 low enough to avoid excess damage to the tissue adjacent distal tip 18. Preferably, current-limiting device 24 keeps current flow through electrode 12 no greater than 20 milliamps in magnitude even when the voltage across current-limiting device 24 approaches 1500 volts in magnitude. Furthermore current-limiting device 24 must have a low enough voltage drop at normal pacing current, for example less than 1 volt at 10 milliamps current, to allow pacemaker assembly 10 to continue to apply a sufficiently high pulse to distal tip 18 to stimulate the adjacent cardiac muscle tissue.

The presence of current-limiting device 24 also permits reduction in the current capacity requirements of diode 20. For example, while diode 20 typically must be capable of handling current loads on the order of one to five amperes in the absence of current-limiting device 24, with device 24 the current capacity of diode 20 may be greatly reduced. Diode 20 may, therefore, even be included in the integrated circuitry of pulse generator 14. Current-limiting device 24 may comprise a current-limiting diode 26 as illustrated in FIG. 5.

Another example of a suitable current-limiting device 24 is illustrated in FIG. 2 as comprising a symmetrical depletion mode field effect device, numbered generally as 30. Device 30 is in effect two field effect transistors connected in series. Device 30 may comprise an N-type substrate 32 as illustrated or, in the alternative, may comprise a P-type substrate. Device 30 as illustrated includes first and second gates 34 and 36, respectively, which are coupled to the respective outside electrodes of device 30 by shorts 38 and 40.

The operation characteristics of device 30 are illustrated in FIG. 3., in which, as shown, device 30 passes a maximum of 20 milliamps current in the presence of up to 1500 volts.

Another suitable example of current limiting device 24 is illustrated in FIG. 4 as comprising the emitter-collector path of transistor 50 in series circuit with diode 52. The base of transistor 50 is coupled to the indifferent terminal of pacemaker 10 or ground through resistor 54 while the emitter of transistor 50 is also coupled to the indifferent terminal of pacemaker 10 or ground by resistor 56. The elements of current-limiting device 24 illustrated in FIG. 4 preferably comprise the following values:

Transistor 50: BU208A
Diode 52: TD15
Resistor 54: 2K ohms
Resistor 56: 10K ohms

Both transistor 50 and diode 52 must have voltage ratings beyond the largest voltage expected to be observed between electrode 12 and pacemaker assembly 10.

Additional advantages and modifications will readily occur to those skilled in the art. The invention in its broader aspects is therefore not limited to the specific details, representative apparatus, and illustrative examples shown and described. Accordingly, departures may be made from such details without departing from the spirit or scope of applicant's general inventive concept.

I claim:

1. In a pacemaker assembly comprising pulse-generator means for generating electrical pulses and electrode means having a proximal end coupled to said pulse-generating means and a distal end designed to be placed adjacent to body tissue for delivering said pulses to said tissue, the improvement comprising:

current-limiting means coupled in series with said pulse-generating means and said electrode means for permitting passage of said electrical pulses to said tissue and for protecting said tissue against tissue damaging current flow between said distal end of said electrode means and said tissue as may occur with cardioversion.

2. The improvement of claim 1 wherein said current-limiting device comprises a current-limiting diode.

3. The improvement of claim 1 wherein said current-limiting device comprises a series connected pair of FET's.

4. The improvement of claims 1 wherein said current-limiting device comprises a transistor and a diode, with the emitter-collector path of said transistor in series with said diode.

5. The improvement of claim 1 wherein said current-limiting device includes at least one semiconductor junction which limits current flow between said distal end of said electrode means and said tissue to 20 mA even when voltage applied to the exterior of said pacemaker assembly is as great as 1500 volts.

6. A protection device for pacemaker implantees comprising pacemaker means for generating electrical pulses, said pacemaker means including a pulse generator for supplying pulses to a proximal end of an electrode, said electrode having a distal end designed to be placed adjacent to body tissue for delivery of said pulses to said tissue; and means coupled between said pulse generator and said electrode for protecting said tissue against all current flow in excess of about 20 milliamperes between said distal end of said electrode and said tissue.

* * * * *